(12) United States Patent
Russell

(10) Patent No.: US 10,172,847 B2
(45) Date of Patent: Jan. 8, 2019

(54) METHOD FOR REDUCING, INHIBITING, AND ELIMINATING INFLAMMATION AND PAIN WITH TRANSDERMAL DELIVERY OF IRON CHELATOR COMPOSITION

(71) Applicant: Kenneth Russell, Austin, TX (US)

(72) Inventor: Kenneth Russell, Austin, TX (US)

( * ) Notice: Subject to any disclaimer, the term of this patent is extended or adjusted under 35 U.S.C. 154(b) by 0 days.

(21) Appl. No.: 15/154,671

(22) Filed: May 13, 2016

(65) Prior Publication Data

US 2017/0326132 A1 Nov. 16, 2017

(51) Int. Cl.
*A61K 31/4704* (2006.01)
*A61K 9/00* (2006.01)
*A61K 31/4045* (2006.01)
*A61K 31/164* (2006.01)
*A61K 31/4196* (2006.01)
*A61K 31/4412* (2006.01)
*A61K 31/426* (2006.01)
*A61K 31/198* (2006.01)

(52) U.S. Cl.
CPC ........ *A61K 31/4704* (2013.01); *A61K 9/0014* (2013.01); *A61K 31/164* (2013.01); *A61K 31/198* (2013.01); *A61K 31/4045* (2013.01); *A61K 31/4196* (2013.01); *A61K 31/426* (2013.01); *A61K 31/4412* (2013.01)

(58) Field of Classification Search
CPC ............ A61K 31/4704; A61K 31/4412; A61K 31/426; A61K 31/4196; A61K 31/198; A61K 31/164; A61K 31/4045
See application file for complete search history.

(56) References Cited

U.S. PATENT DOCUMENTS

| | | | | |
|---|---|---|---|---|
| 5,318,960 A | * | 6/1994 | Toppo | A61K 9/0014 514/159 |
| 6,899,667 B2 | * | 5/2005 | Becker | A61N 2/008 336/122 |
| 8,309,081 B2 | * | 11/2012 | Studin | A61K 36/15 424/94.65 |
| 9,969,812 B2 | * | 5/2018 | Sakamoto | C07K 16/32 |
| 2010/0035992 A1 | * | 2/2010 | Bhushan | A61K 31/10 514/566 |

* cited by examiner

*Primary Examiner* — Jennifer M Kim
(74) *Attorney, Agent, or Firm* — Frank Huy Pham; Pham IP group

(57) ABSTRACT

A method for reducing, inhibiting, and eliminating inflammation and pain by using an effective amount of iron chelator composition to balance oxidative activity at a cutaneous site of inflammation and pain. The composition contained in transdermal formulations and administered topically in accordance with the invention can be combined with one or more suitable carriers and can be administered in conjunction with one or more additional therapeutic agents.

3 Claims, No Drawings

METHOD FOR REDUCING, INHIBITING, AND ELIMINATING INFLAMMATION AND PAIN WITH TRANSDERMAL DELIVERY OF IRON CHELATOR COMPOSITION

BACKGROUND

1. Field of the Invention

This invention is related to the use of an effective amount of iron chelator composition and other therapeutic agents in the reduction, inhibition, and elimination of inflammation and pain.

2. Description of the Prior Art

Inflammation is a biological response that can result from a noxious stimulus and is normally intended to remove that stimulus or ameliorate its effects. Although normally intended to promote survival, inflammation can cause damage to the host.

Inflammation has been classified as acute and chronic. Acute inflammation is typically of relatively short duration, lasting minutes to hours and, in some cases, a few days. Acute inflammation can be characterized by the exudation of fluid and plasma proteins and the accumulation of polymorphonuclear leukocytes (PMNLs) at the site of the insult. Acute inflammation usually includes an increase in blood flow to the area of the insult mediated by cellular molecules released in response to the insult. Increased vascular permeability also results from cellular mediators and leads to an accumulation of protein-rich fluid. Important mediators of this increased blood flow and vascular permeability include histamine from mast cells, serotonin and bradykinin.

In acute inflammation, PMNLs are also attracted to the area of insult and migrate out of the blood stream toward the insult. The PMNLs release toxic metabolites and proteinases that can cause tissue damage. These proteinases include proteins in the complement system, which can damage cell membranes and kallikreins which generate bradykinin. Acute inflammation can undergo complete resolution, lead to the formation of an abscess, result in scarring fibrosis or progress to chronic inflammation.

Chronic inflammation is a longer duration, lasting weeks to months, and possibly years, in which tissue destruction and biological processes that are intended to repair the injury are simultaneously ongoing. Chronic inflammation more typically involves lymphocytes and macrophages and may also include a proliferation of blood vessels, fibrosis and/or necrosis. Chronic inflammation can result from a number of conditions including persistent infections, prolonged exposure to toxic agents, and autoimmune reactions. Chronic inflammation is often maintained by the production of cytokines by lymphocytes and macrophages at the site of the persistent insult. Chronic inflammation can result in permanent tissue damage or complete healing.

Inflammatory responses in the peripheral and central nervous systems play key roles in the development and persistence of many pathological pain states. Certain inflammatory cytokines in spinal cord, dorsal root ganglion (DRG), injured nerve or skin are known to be associated with pain behaviors and with the generation of abnormal spontaneous activity from injured nerve fibers or compressed/inflamed DRG neurons.

One of the cardinal features of inflammatory states is that normally innocuous stimuli produce pain. It has been widely appreciated that the nervous system exhibits a range of responses according to different conditions ('neural plasticity'). Subsequent research has characterized the mechanisms by which these changes occur and highlighted the importance of environmental factors on perception of pain.

Cytokines play an important role in the initiation and maintenance of inflammatory diseases as mediators of cell-cell interactions. In addition to their enhancing and inhibitory effects on immune and inflammatory cells, cytokines exert considerable influence over sensory neurones. Similar to other mediators, cytokines may act directly on nociceptors or, more commonly, indirectly, stimulating the release of agents such as prostaglandins. During acute phases, cytokines appear to induce sensitization via receptor-associated kinases and phosphorylation of ion channels whereas in chronic inflammation transcriptional up-regulation of receptors and secondary signalling become more important.

Inflammation and pain can be determined in a number of ways. Determinations can be made by measuring IL-1beta and transforming growth factor levels (TGF) wherein an increase in either or both of these factors corresponds to a decrease in anti-inflammatory cytokine activity.

The anti-inflammatory cytokines are a series of immunoregulatory molecules that control the pro-inflammatory cytokine response. Cytokines act in concert with specific cytokine inhibitors and soluble cytokine receptors to regulate the human immune response. Their physiologic role in inflammation and pathologic role in systemic inflammatory states are increasingly recognized. Major anti-inflammatory cytokines include interleukin (IL)-1 receptor antagonist, IL-4, IL-10, IL-11, and IL-13. Leukemia inhibitory factor, interferon-alpha, IL-6, and transforming growth factor (TGF)-β are categorized as either anti-inflammatory or pro-inflammatory cytokines, under various circumstances. Specific cytokine receptors for IL-1, TNF-α, and IL-18 also function as inhibitors for pro-inflammatory cytokines.

Measurement indicating anti-inflammatory cytokine activity is the determination of immune cell infiltration, such as the presence of polymorphonuclear neutrophils or macrophages. A decrease in these cell types indicates an anti-inflammatory response and vice versa.

Pro-inflammatory cytokines are produced predominantly by activated macrophages and are involved in the up-regulation of inflammatory reactions. Macrophages maintain sufficient supply of iron for erythropoiesis and an increase of IL-1beta promotes efficient iron storage within macrophages or monocytes by increasing the expression of ferritin, both at the transcriptional and posttranscriptional level.

Certain inflammatory cytokines are also involved in nerve-injury/inflammation-induced central sensitization, and are related to the development of contralateral hyperalgesia/allodynia. The discussion presented in the present invention describes several key pro-inflammatory cytokines and anti-inflammatory cytokines, their relation with pathological pain in human patients, and possible underlying mechanisms.

Independently of the inducing factor—and the length of the exposure—an inflammatory reaction is mediated by a varied number and type of cells and molecules, the later including cytokines, growth factors, clotting factors, enzymes, neurotransmitters and complement proteins, among others. These molecules are primarily secreted by fibroblasts, endothelial and infiltrating cells (e.g. macrophages, lymphocytes, mast cells, polymorphonuclear cells, etc), and local nerves in response to the insulting agent. The mixture and amount of cytokines therein released will depend on the type, concentration and exposure time of the inducing agent. Therefore, these proteins could mediate from an acute local inflammatory reaction to systemic life-threatening responses (e.g. acute systemic inflammatory response syndrome, SIRS; multiple organ failure as in septic shock; anaphylaxis, etc). In chronic inflammatory processes, the cytokines continuously recruit more and more infiltrating cells that generate, for example, granulomas, induration of the tissues, and encapsulated abscesses. In any case, proteins secreted during an inflammatory process are central players in the grade and persistence of the final reaction.

The systemic inflammatory response syndrome (SIRS), a syndrome that encompasses the features of systemic inflammation without end-organ damage or identifiable bacteremia. SIRS is separate and distinct from sepsis, severe sepsis or septic shock. The key transition from SIRS to sepsis is the presence of an identified pathogen in the blood. The pathophysiology of SIRS includes, but is not limited to, complement activation, cytokine and arachidonic acid metabolites secretion, stimulated cell-mediated immunity, activation of the clotting cascades, and humoral immune mechanisms. Clinically SIRS is characterized by tachycardia, tachypnea, hypotension, hypoperfusion, oliguria, leukocytosis or leukopenia, pyrexia or hypothermia, metabolic acidosis, and the need for volume support. SIRS may affect all organ systems and may lead to multiple organ dysfunction syndrome (MODS). Thus, even in early stages (i.e. SIRS), there is accumulation of pro-inflammatory cytokines at the primary site of inflammation and in the blood that can contribute to the establishment of multi-organ failure and death.

Inflammation can also be determined by the concentration of iron at an inflammatory site. High iron concentration may amplify the damaging effects of superoxide overproduction in a very broad spectrum of inflammatory, both acute and chronic conditions.

Iron overload may amplify the damaging effects of superoxide overproduction in a very broad spectrum of inflammatory, both acute and chronic, conditions. Furthermore, chronic oxidative stress may modulate iron uptake and storage, leading to a self-sustained and ever increasing spiral of cytotoxic and mutagenic events.

Iron chelator composition is able to chelate 'free iron' even inside the cell. Its regular clinical use is to promote the excretion of an iron overload, when phlebotomy is harmful, and the dosage varies between 2-10 g/d. In conditions where melatonin is used to prevent the iron-driven oxygen toxicity, i.e., acute or chronic inflammatory diseases with oxidative stress, the dosage can be extremely reduced and the addition of antioxidants could be useful.

Mechanical and thermal hypersensitivity assays can also be used to determine pain sensitivity. The assays can detect increases and decreases in sensitivity to pain.

Typically, inflammation is treated with steroidal or non-steroidal anti-inflammatory drugs. However, conventional anti-inflammatory therapy suffers from several drawbacks, e.g., systemic toxicity, allergic reactions, insulin resistance, hypertension, cardiac toxicity, renal toxicity, various coagulopathies and gastric erosions. Accordingly, there is a need for mild, yet safe and effective methods for reducing, inhibiting, and eliminating inflammation.

The present invention provides such methods. These and other advantages of the invention, as well as additional inventive features, will be apparent from the description of the invention provided herein.

Many substances are applied topically to the skin or mucous membranes of humans or animals (hereinafter "skin") in order to alter the subject's appearance, to protect the subject from the environment, or to produce a biological change in the skin or other tissue for therapeutic, preventive or cosmetic purposes. These substances may generically be termed "topical products" and include such topically applied substances as cosmetics, over-the-counter and prescription topical drugs, and a variety of other products such as soaps and detergents.

Topical products occur in a variety of forms, including solids, liquids, suspensions, semisolids (such as creams, gels, lotions, pastes or "sticks"), powders or finely dispersed liquids such as sprays or mists. Examples of topical products commonly classified as "cosmetics" include skin care products such as moisturizing creams and lotions, and "treatment cosmetics" such as exfoliants and/or skin cell renewal agents; fragrances such as perfumes and colognes, and deodorants; shaving-related products such as creams, "bracers" and aftershaves; depilatories and other hair removal products; skin cleansers, toners and astringents; pre-moistened wipes and washcloths; tanning lotions and sunscreens; bath products such as oils; eye care products such as eye lotions and makeup removers; foot care products such as powders and sprays; skin colorant and make-up products such as foundations, blushes, rouges, eye shadows and liners, lip colors and mascaras; lip balms and sticks; hair care and treatment products such as shampoos, conditioners, colorants, dyes, bleaches, straighteners, and permanent wave products; baby products such as baby lotions, oils, shampoos, powders and wet wipes; feminine hygiene products such as deodorants and douches; skin or facial peels applied by dermatologists or cosmeticians; and others.

Many topical formulations contain chemical emulsions which use surface active ingredients (emulsifiers) to disperse dissimilar chemicals in a particular solvent system. For example, most lipid-like (oily or fatty) or lipophilic ingredients do not uniformly disperse in aqueous solvents unless they are first combined with emulsifiers which form microscopic aqueous soluble micelles that contain a lipid-soluble interior and an aqueous-soluble exterior, resulting in an oil-in-water emulsion. In order to be soluble in aqueous media, a molecule must be polar or charged so as to favorably interact with water molecules which are also polar. Similarly, to dissolve an aqueous-soluble polar or charged ingredient in a largely lipid or oil-based solvent, an emulsifier is typically used which forms stable micelles that contain the aqueous soluble components in the micelle interior while the exterior of the micelle is lipophilic so that it can dissolve in the lipophilic solvent to form a water-in-oil emulsion. It is well known that such emulsions can be destabilized by the addition of salts or other charged ingredients which can interact with the polar or charged portions of the emulsifier within an emulsion micelle. Emulsion destabilization results in the aqueous and lipophilic ingredients separating into two layers, potentially destroying the commercial value of a topical product. Because the aqueous-soluble strontium cation has two positive charges, it is especially disruptive of emulsion systems compared to ions with only one positive charge (e.g., sodium ions). The concentrations of strontium salts, particularly strontium nitrate, in many of the topical formulations of the present invention that provide an optimum consumer benefit (e.g., anti-irritant properties) are approximately 4-6% 35 w/w (approximately 190-280 mM). In this concentration range many common emulsion systems become unstable and separate into their two phases. The formulations of the invention have overcome the inherent tendency of high salt concentrations in general, and high strontium salt concentrations in particular, to destabilize emulsions.

In addition to destabilizing emulsions, formulations with high salt concentrations often precipitate out other ingredients commonly found in topical product formulations like cosmetics and topical therapeutics. Many factors such as pH, choice of solvent, active ingredients, preservatives, and the number and concentrations of many other ingredients may cause salts to precipitate and form crystals, thus reducing or destroying the value of the product. The process of "salting out" proteins and other aqueous-soluble chemicals is well known in the art to be a problem with solutions containing high salt concentrations. The formulations of the present invention have overcome the inherent tendency of high salt concentrations in general, and high strontium salt concentrations in particular, to precipitate ingredients in topical formulations.

One of the most important aspects of topical products in general, and cosmetic products in particular, is the consumer's perception of the aesthetic qualities of a product. For example, while petrolatum (e.g., Vaseline™) is an excellent "moisturizer" and skin product, it is rarely used alone, especially on the face, because it is greasy, sticky, does not rub easily into the skin and may soil clothing. Consumers highly value products which are aesthetically elegant and have an acceptable tactile feel and performance on their skin. Formulations with high salt concentrations frequently have relatively poor aesthetics due to their unfavorable effects on the other ingredients of the formulation. The formulations of the present invention have overcome the inherent tendency of high salt concentrations in general, and high strontium salt concentrations in particular, to produce aesthetically poor products.

Examples of topical products commonly classified as "topical drugs" are many and varied, and include over-the-counter and/or prescription products such as antiperspirants, insect repellents, sunscreens and sunburn treatments, anti-acne agents, antibiotics, therapeutic retinoids, anti-dandruff agents, external analgesics such as capsaicin products, topical contraceptives, topical drug delivery systems, suppositories and enemas, hemorrhoid treatments, vaginal treatments, lozenges, and many other products with therapeutic or other effects. Other topical products include hand, facial and body soaps and detergents and other forms of skin cleansers, as well as household detergents and many other household products such as solvents, propellants, polishes, lubricants, adhesives, waxes and others which are either applied topically or are topically exposed to the body during normal use.

Certain divalent cautions including magnesium and calcium in transdermal formulations have long been reported in laboratory studies to have a "depressant" effect on nerves, clinical studies have shown that intravenously-administered magnesium sulfate produces neither anesthesia nor even analgesia in humans (Kato et al., Can. Anaes. Soc. J. 15, 539-544 (1968)). Instead, the magnesium ion induces paralysis of skeletal muscles, due perhaps to the inhibitory effects of magnesium on muscle cell activity. Oral ingestion of large doses of magnesium (e.g., magnesium sulfate as a laxative) does not result in paralysis or depressed neural activity in healthy individual also. On the other hand, when magnesium is applied directly to the brains of test animals, depressed neural or synaptic activity, and even a sleep-like state, reportedly result.

Another complicating factor arises from the detailed nature of nerve cell activity and response. The firing activity of an individual nerve cell may be influenced in a complex fashion, and may vary over time, depending on such factors as the extracellular and intracellular concentration of nerve-related ions as sodium, potassium, chloride, calcium and the like, as well as the time course of exposure to such ions. Other bioactive agents, such as prostaglandins present during inflammatory responses, may further influence nerve sensitivity. In addition, nerves may respond to non-chemical stimuli such as hydrodynamic pressure changes, which in turn may depend on the nature of the tissue in which the nerve is disposed. Such factors lead to considerable clinical uncertainty as to how various agents may affect such nervous responses.

Accordingly, it is desirable to identify agents which are effective in the skin to inhibit certain identified sensory responses (as for example burn, sting, or itch) while not adversely affecting other nervous responses in the same tissue (as for example tactual sensations), and to include such anti-irritant agents in topical product formulations.

Thus, an aspect of the present invention is to provide topical product formulations that comprise a composition of iron chelation at a concentration effective amount to reduce, inhibit, and eliminate inflammation and pain.

SUMMARY OF THE INVENTION

The present invention provides a method of reducing, inhibiting, and eliminating inflammation and pain in a patient by administering a therapeutically effective amount of iron chelator composition to modulate oxidative activity at a cutaneous site of inflammation and pain.

One objective of the present invention can be used in the treatment of inflammation resulting from a variety of causative factors, e.g., allergic reaction, autoimmune reaction, infection, contact with one or more inflammation-causing substances, and combinations of such causative factors.

A preferred embodiment of the present invention includes administering the iron chelator composition in conjunction with one or more therapeutic agents, e.g., one or more compounds selected from the group consisting of anti-viral agents, anti-inflammatory agents, and combinations thereof. Administering such therapeutic agents in conjunction with the iron composition includes administering one or more of such agents, e.g., prior to, during (e.g., contemporaneously, by co-administration or in combination with), or following administration of the composition.

A preferred embodiment of the present invention providing the administration of the iron chelator composition in accordance with the present invention is preferably to a cutaneous site of inflammation or potential inflammation. The administration of the composition can be in conjunction with transdermal formulations applied directly to the cutaneous site.

A preferred embodiment of the present invention provided herein is directed to the administration of the iron chelator composition for reducing, inhibiting, and eliminating pain associated with the inflammation. The method comprises the administration of iron chelator composition to an individual in an amount effective to reduce, inhibit, and eliminate the pain.

A preferred embodiment of the present invention is directed to topical transdermal formulations as a delivery vehicle containing the lipophilic, hydrophilic and surfactant components and aqueous oil based solution thereof as ingredients to provide fast, efficient, and safe topical skin penetration through the stratum corneum of human skin.

A preferred embodiment of the present invention is further directed to one object of the present invention to provide the topical transdermal formulations and ingredients in emulsions which can suppress skin irritation due to tissue inflammation. However, the invention is particularly useful for reducing, inhibiting, and eliminating the inflammation and pain caused by the increase of macrophage iron at the site of the injury or infection.

A preferred embodiment of the present invention further provides vehicles and vehicle components that are especially useful in the transdermal formulations, as well as concentration ranges and processing steps to obtain useful formulation forms including solids, creams, lotions, gels, and liquids.

The present invention further provides objects and advantages that will become apparent from a description of the several embodiments as set forth in the following description.

DETAILED DESCRIPTION

The method of the present invention provides a method of reducing, inhibiting, and eliminating inflammation and pain in a patient, which method comprises administering to the patient a therapeutically effective amount of an iron chelator composition, wherein the composition is contained in the topical transdermal formulations.

The method of the present invention can be used for reducing, inhibiting, and eliminating (e.g., inhibiting the onset of, inhibiting the escalation of, decreasing the likelihood of acute inflammation and chronic inflammation). The inflammation treatable or preventable in accordance with the method of the present invention can include inflammation that results from, e.g., contact with a noxious stimulus, injury, infection, autoimmune reaction, and allergic reaction, including allergic reactions associated with cellular histamine and pro-inflammatory cytokine release.

The method of the present invention providing the administration of the iron chelator composition can be in combination with one or more further therapeutic agents and includes simultaneous (concurrent) and consecutive administration in any order. The regulation or administration of the composition can occur after induction of inflammation or pain, but preferably occurs simultaneously with induction of inflammation and pain. The induction of inflammation and/or pain can be the result of sports-related activities, hard labor, blister, repetitive trauma inducing activities or the undertaking of surgery.

The method of the present invention providing the administration of the iron composition can also be administered to an individual having rheumatoid arthritis to reduce swelling and pain associated with arthritis. Generally, inflammatory disorders include any disorder or condition associated with inflammation, i.e., inflammation of the bowel or any other organ, chemically induced inflammation, inflammation due to repetitive trauma. Each of these conditions, disorders, injuries or inflictions is encompassed by the phase insult resulting in inflammation or pain The method of the present invention providing the administration of the iron composition refers inhibition as used herein refers to any delay in the onset of a condition, particularly inflammation or pain. The reduction as used herein refers to a decrease of at least 10%, and more preferably at least a 25% decrease in activity is preferred, with at least about 50% being particularly preferred and about a 95-100% decrease being especially preferred.

The method of the present invention providing the administration of the iron composition further comprises an iron chelator wherein the iron chelator is selected from the group comprising M30, melatonin, deferoxamine (DFO), deferasirox, deferiprone, deferitrin, L1NAII, CP502, IOX2, IP6, ethylenediaminetetraacetic acid (EDTA) or combinations thereof. In the most preferred embodiment, the iron chelator is melatonin.

The method of the present invention providing the administration of the iron composition for the reduction, inhibition, and elimination of inflammation and pain wherein the inhibition as used herein refers to any delay in the onset of a condition, particularly inflammation or pain. Reduction as used herein refers to a decrease of at least 10%, and more preferably at least a 25% decrease in activity is preferred, with at least about 50% being particularly preferred and about a 95-100% decrease being especially preferred. The reduction is compared to a control concentration of administration of the biologically active composition, wherein the control concentration can be zero.

The method of the present invention providing the administration of the iron composition reduces an elevation of IL-1beta by at least 30%, preferably 40%, more preferably 50%, still more preferably 60% and most preferably 70-100%.

The method of the present invention providing the administration of the iron composition suppresses the activation of macrophages and reduces an elevation of IL-1beta level by at least 30%, preferably 40%, more preferably 50%, still more preferably 60% 30 and most preferably 70-100%.

The method of the present invention providing the administration of the iron composition, via topical transdermal formations, reduces macrophage iron infiltration in response to an inflammatory stimulus. In an embodiment herein, the macrophage iron infiltration is decreased as it is seen in a normal individual in response to an inflammatory stimulus.

The method of the present invention providing the administration of the iron chelator composition wherein the composition is for chelating free iron inside the cell and therefore preventing the iron-driven oxygen toxicity i.e., acute or chronic inflammatory diseases with oxidative stress.

The method of the present invention providing the administration of the iron chelator composition applies in anticipation of pain, independent of an inflammatory inducing agent. In this embodiment, thermal sensitivity measured in withdrawal time can be reduced.

The method of the present invention providing the administration of the iron chelator composition wherein the composition can be formulated according to known methods to prepare pharmaceutically useful compositions. By way of example, the pharmaceutical compositions can be formed by combining composition in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of aqueous oil based solutions.

The method of the present invention providing the administration of the iron chelator composition further provides acceptable carriers, excipients or stabilizers are nontoxic to recipients at the dosages and concentrations employed, and include buffers such as antioxidants including ascorbic acid; low molecular weight (less than about 10 residues) polypeptides; hydrophilic polymers such as polyvinyl pyrrolidone; chelating agents such as EDTA; and/or nonionic surfactants such as Tween, Pluronics or PEG. Transdermal formulations are particularly preferred for an efficient and quick delivery method of active agent to targeted location system locally or systematically.

The method of the present invention providing the administration of the iron chelator composition wherein dosages and desired drug concentrations of pharmaceutical compositions of the present invention may vary depending on the particular use envisioned. The determination of the appropriate dosage or route of administration is well within the skill of an ordinary physician.

The method of the present invention providing the administration of the iron chelator composition wherein modulators that enhance the anti-inflammatory and pain reduction activity of cytokine can be identified and administered to an individual in need thereof in conjunction with or independently iron chelator composition. Modulation is a change of about at least 10-30%, preferably 40-50%, more preferably at least 50-75%, or most preferably, at least 75-100%. As discussed herein, changes in cytokine activities can be determined by identification of changes in pain and inflammation responses. Such responses can be determined by identification in changes in the presence of TGF, IL-1beta and immune cell infiltrate as well as mechanical and thermal sensitivity and physical swelling.

The method of the present invention providing the administration of the iron chelator composition wherein the transdermal formulations overcome several difficult problems inherent in incorporating high concentrations (greater than about 2% w/w) of aqueous-soluble, charged inorganic salts (e.g., strontium salts) into aesthetic (e.g., pleasant-feeling, elegant, etc.) and functionally active topical products (i.e., products which retain their cosmetic, therapeutic, or other functional characteristics).

The method of the present invention providing the administration of the iron chelator composition wherein the composition is contained in the transdermal formulations that are miscible and will remain in solution. Consequently, in accordance with the inventive method, the transdermal formulations can be conveniently applied to the skin in the area of pain and inflammation by spaying or misting, or by any other desired liquid application technique. The application can then be reapplied as needed up to as often as once every 1-3 hours.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above described exemplary embodiments, but should be defined only in accordance with the following claims appended hereto and their equivalents.

Having illustrated and described the principles of the present invention in a preferred embodiment, it will be apparent to those skilled in the art that the embodiment can be modified in arrangement and detail without departing from such principles. Any and all such embodiments are intended to be included within the scope of the following claims.

What is claimed is:

1. A method for reducing, inhibiting, and eliminating pain associated with inflammation in a patient, the method comprising transdermally administering to an area of skin a composition to balance oxidative activity at a cutaneous site of inflammation and pain, said composition comprising (a) melatonin, aspirin, deferoxamine, ethylenediaminetetraacetic, and IP6; and (b) antioxidant buffers, wherein antioxidant is ascorbic acid.

2. The method of claim 1, wherein
   (a) said composition is in a form selected from the group consisting of liquid, cream, gel, spray, lotion; and
   (b) said composition exerts a transdermal effect following said topical administration.

3. The method of claim 1, wherein said transdermal formulation further comprises of carriers, excipients, stabilizers, nonionic surfactants, and lipophilic for enhancing skin penetration.

* * * * *